United States Patent
Roessler et al.

(10) Patent No.: US 6,884,310 B2
(45) Date of Patent: Apr. 26, 2005

(54) METHOD FOR MAKING AN ABSORBENT ARTICLE WITH ELASTIC CUFF AREAS AND EXPANDABLE SUBSTRATES

(75) Inventors: Thomas Harold Roessler, Menasha, WI (US); Michael Tod Morman, Alpharetta, GA (US); Paul Theodore Van Gompel, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 183 days.

(21) Appl. No.: 10/024,988

(22) Filed: Dec. 19, 2001

(65) Prior Publication Data

US 2003/0114826 A1 Jun. 19, 2003

(51) Int. Cl.⁷ .................................................. A61F 13/15
(52) U.S. Cl. ........................ 156/229; 156/161; 156/163; 156/164
(58) Field of Search ................................ 156/161, 163, 156/164, 229, 494–496

(56) References Cited

U.S. PATENT DOCUMENTS

| 4,055,182 A | 10/1977 | Mack |
| 4,239,578 A | 12/1980 | Gore |
| 4,364,787 A | 12/1982 | Radzins |
| 4,379,016 A | 4/1983 | Stemmler et al. |
| 4,381,781 A | 5/1983 | Sciaraffa et al. |
| 4,397,704 A | 8/1983 | Frick |
| 4,407,284 A | 10/1983 | Pieniak |
| 4,464,217 A | 8/1984 | Dickover et al. |
| 4,515,595 A | 5/1985 | Kievit et al. |
| 4,543,154 A | * 9/1985 | Reiter .................... 156/229 |
| 4,606,964 A | * 8/1986 | Wideman .................... 156/164 |
| 4,618,384 A | 10/1986 | Sabee |
| 4,663,220 A | 5/1987 | Wisneski et al. |
| 4,704,116 A | 11/1987 | Enloe |

(Continued)

FOREIGN PATENT DOCUMENTS

| EP | 217 032 | 4/1987 |
| EP | 417 766 | 3/1991 |

(Continued)

Primary Examiner—Jeff H. Aftergut
(74) Attorney, Agent, or Firm—David J Arteman; Alyssa A Dudkowski (57) ABSTRACT

The present invention provides a method of achieving selectively elasticized zones on nonwoven web substrates, such as may be suitable for the waistbands of disposable absorbent pant garments, cuffs on sleeves of medical garments, or the like. A web, or webs, of nonwoven material which make up the substrate for the elasticized area are provided to be inherently extendable in the transverse, or lateral, direction of the material web at the time the elastic material is affixed to the substrate. If the elastic material is affixed in an untensioned state, a flat waistband without gathering of the substrate may be had for a very efficient seal against the skin of the wearer. If the elastic material is affixed to the substrate in a tensioned state, a waist band with gathering of the substrate may be had to allow for two-stage expansion via the gathers and the expansion of the substrate.

6 Claims, 5 Drawing Sheets

U.S. PATENT DOCUMENTS

| | | | |
|---|---|---|---|
| 4,710,189 A | | 12/1987 | Lash |
| 4,798,603 A | | 1/1989 | Meyer et al. |
| 4,808,176 A | | 2/1989 | Kielpikowski |
| 4,813,946 A | | 3/1989 | Sabee |
| 4,816,026 A | | 3/1989 | Richardson |
| 4,834,741 A | | 5/1989 | Sabee |
| 4,895,568 A | * | 1/1990 | Enloe .................... 604/385.27 |
| 4,908,247 A | * | 3/1990 | Baird et al. ................. 156/164 |
| 4,917,682 A | * | 4/1990 | Lancaster et al. ........ 604/385.3 |
| 4,925,520 A | | 5/1990 | Beaudoin et al. |
| 4,938,753 A | | 7/1990 | Van Gompel et al. |
| 4,938,821 A | | 7/1990 | Soderlund et al. |
| 4,965,122 A | | 10/1990 | Morman |
| 4,968,313 A | | 11/1990 | Sabee |
| 5,167,897 A | | 12/1992 | Weber et al. |
| 5,176,668 A | | 1/1993 | Bernardin |
| 5,176,672 A | | 1/1993 | Bruemmer et al. |
| 5,192,606 A | | 3/1993 | Proxmire et al. |
| 5,226,992 A | | 7/1993 | Morman |
| 5,254,111 A | | 10/1993 | Cancio et al. |
| 5,340,424 A | | 8/1994 | Matsushita |
| 5,364,382 A | | 11/1994 | Latimer et al. |
| 5,399,219 A | | 3/1995 | Roessler et al. |
| 5,405,342 A | | 4/1995 | Roessler et al. |
| 5,407,507 A | | 4/1995 | Ball |
| 5,415,644 A | | 5/1995 | Enloe |
| 5,429,629 A | | 7/1995 | Latimer et al. |
| 5,486,166 A | | 1/1996 | Bishop et al. |
| 5,490,846 A | | 2/1996 | Ellis et al. |
| 5,496,298 A | | 3/1996 | Kuepper et al. |
| 5,509,915 A | | 4/1996 | Hanson et al. |
| 5,531,729 A | | 7/1996 | Coles et al. |
| 5,540,796 A | | 7/1996 | Fries |
| 5,595,618 A | | 1/1997 | Fries et al. |
| 5,649,919 A | | 7/1997 | Roessler et al. |
| 5,683,531 A | | 11/1997 | Roessler et al. |
| 5,700,255 A | | 12/1997 | Curro et al. |
| 5,743,994 A | * | 4/1998 | Roessler et al. ............ 156/495 |
| 5,827,259 A | | 10/1998 | Laux et al. |
| 5,846,232 A | | 12/1998 | Serbiak et al. |
| 5,910,224 A | | 6/1999 | Morman |
| 6,050,985 A | | 4/2000 | Lavon et al. |
| 6,077,254 A | | 6/2000 | Silwanowicz et al. |
| 6,093,178 A | * | 7/2000 | Osborn et al. .............. 604/387 |
| 6,156,421 A | | 12/2000 | Stopper et al. |
| 6,183,847 B1 | | 2/2001 | Goldwasser |
| 6,231,557 B1 | | 5/2001 | Krautkramer et al. |
| 6,245,050 B1 | | 6/2001 | Odorzynski et al. |
| 6,264,641 B1 | | 7/2001 | Van Gompel et al. |
| 2003/0114817 A1 | | 6/2003 | Roessler et al. |
| 2003/0114825 A1 | | 6/2003 | Morman et al. |

FOREIGN PATENT DOCUMENTS

| | | |
|---|---|---|
| EP | 437 771 | 7/1991 |
| EP | 650 714 | 5/1995 |
| EP | 682 930 | 11/1995 |
| EP | 750 893 | 1/1997 |
| EP | 820 747 | 1/1998 |
| EP | 1 179 330 | 2/2002 |
| EP | 1 188 427 | 3/2002 |
| EP | 1 228 741 | 8/2002 |
| WO | 95/16425 | 6/1995 |
| WO | WO-95/19258 A1 * | 7/1995 |
| WO | WO 96/10481 | 4/1996 |
| WO | WO 00/38911 | 7/2000 |
| WO | WO 01/15646 A1 | 3/2001 |
| WO | 01/91685 | 12/2001 |
| WO | 01/92013 | 12/2001 |

* cited by examiner

METHOD FOR MAKING AN ABSORBENT ARTICLE WITH ELASTIC CUFF AREAS AND EXPANDABLE SUBSTRATES

BACKGROUND OF THE INVENTION

Field of the Invention

It is desired that absorbent articles, and especially garments such as diapers, training pants or incontinence garments, without limitation referred to generically now for ease of explanation as "diapers", provide a close, comfortable fit about the waist of the wearer and contain body exudates while maintaining skin health. In certain circumstances, it is also desirable that such garments are capable of being pulled up or down over the hips of the wearer to allow the wearer or care giver to easily pull the article on and easily remove the article. Other garment openings such as sleeve or pant cuffs and necklines may benefit from similar elasticizing.

Various schemes for producing elastic waistbands on disposable diapers have been proposed. Diaper waistbands are generally made by stretching an elastomer, applying the stretched elastomer to the diaper components, typically nonelastic in the waistband area, and allowing the elastomer to retract, thus gathering and shirring the attached diaper web components in the waistband area. The gathered waistband will then ungather to some extent when applied to a wearer, to give the waistband circumference some extension while the elastomer produces a retractive force holding the waistband snug to the wearer. However, this gathered-material waistband arrangement may be esthetically unappealing as looking less like a fully finished cloth garment or functionally deficient as forming channels for the leakage of exudates. Further, manipulation and application of the stretched, or tensioned, elastics to nonwoven webs moving at high speeds is difficult.

In another known method of making elastic waist bands, U.S. Pat. No. 4,968,313 issued Nov. 6, 1990 to Sabee, teaches the application of a relaxed elastic element to a relaxed diaper web component which is subsequently drawn or stretched to change the molecular orientation of the fibers of the web and permanently deform the fiber structure to produce a gathered waist band for the garment.

There further remains a need for other methods of making waistbands for disposable garments which provide ease and economy of manufacture, and adequate performance.

SUMMARY OF THE INVENTION

In response to the above discussion, an alternative method of waistband construction is provided by the present invention which provides improved ease and economy of manufacture, while maintaining adequate fit and improved sealing performance.

The methods of the present invention allow elastomeric materials to be incorporated into the diaper assembly in a simplified fashion. In particular, with most presently practiced methods, elastomeric materials are stretched, cut and held under tension. This type of manipulation of individual pieces of unstable elastomeric materials makes incorporation into a diaper assembly challenging. With the methods of the present invention, the elastomeric materials do not have to be under tension or can be under less tension than is necessary with conventional methods. This makes manipulation of the elastomeric materials easier. For example, the elastomeric materials can be cut, rotated and applied much more easily. Additionally, materials that are elastomeric in the cross-direction can be applied without rotation.

The methods of the invention may involve the application of elastomeric materials in both an untensioned state and a reduced tensioned state. The selection of the tension under which the elastomeric materials are applied depends on how best to insure that the waistband will be flat in use so as to form a good seal. It is desirable to have small circumference of the product at the waist for purposes of forming a good seal with the wearer's body and for purposes of eliminating any gathers or rugosities that could serve as channels for the leakage of body exudates. For example, when manufacturing a diaper to be used on small babies, it may be desirable to apply the elastomeric materials under low tension so that the finished diaper has some gathered material in the waistband. However, when such a diaper is applied to a baby, the waistband is extended by the baby's body, the gathers are removed and the result is a flat waistband against the baby's body during wear. While the desirability of a flat waistband is described, it is also desirable, for the same reasons, to be able to provide flat leg elastics.

The method according to one embodiment of the present invention can provide a flat or ungathered waistband having extensibility and elasticity while looking like a fully finished cloth garment without channels for the leakage of exudates. In other embodiments, any garment opening such as sleeve or leg cuffs or necklines may benefit from similar elasticizing. The margins of any garment opening will hereinafter be collectively referred to as "cuffs" or "cuff areas".

The person having ordinary skill in the art of disposable diaper manufacture will appreciate that the disposable diaper is generally made up of the layers of a substantially liquid-impermeable backsheet, a liquid-permeable topsheet and an liquid retention structure located between the backsheet and the topsheet. In order to be extendable any two joined layers must have compatible stretch to the limits of the desired processing parameters. In other words, the combined layers or webs, in those areas where the webs are fastened together, will be limited in the amount they may be stretched by the properties of the layer having the least amount of stretch.

The present invention presents an alternative way of making an elastomeric cuff area by attaching an elastomer to a cuff area of the precursor garment, or more accurately, a selected component web of the precursor garment. The cuff area components of the present invention are inherently extendible in the necessary dimension of the garment. That is, the selected components do not need to be necked or otherwise physically manipulated with the garment-making apparatus to provide this extensibility. The elastomer can be applied in low tensioned or untensioned conditions to the cuff area of the extendible precursor garment web at high speeds to achieve gathered or flat cuffs, respectively. When the garment is placed on the wearer, the cuff may be physically caused to expand, thus forming a desirable snug fitting and flat cuff area having extendible dimension and elastic tension.

Generally, the present invention is illustrated as a disposable absorbent article such as a diaper, although the skilled artisan will appreciate that the teachings of the present invention may be applied to any type garment with a need for elastomeric cuffs. The diaper defines a front waist section, a rear waist section, an intermediate section which extends between and connects the waist sections, a pair of laterally opposed side edges, a pair of longitudinally opposed waist edges, a longitudinal direction and a lateral direction. Exemplary elastic waistbands for waist sections are provided in a unique manner of the present invention with elasticity to help the waist sections conform to the body of the wearer.

The absorbent article may also include other known components of diapers such as a pair of fasteners located on the laterally opposed side edges in one of the waist sections. In certain aspects, the disposable absorbent article may be provided in a prefastened, pant-like configuration such that the article can be pulled on or off over the hips of the wearer similar to conventional training pants. For example, the fasteners may refastenably attach the laterally opposed side edges in the front waist section to the laterally opposed side edges in the rear waist section to provide the pant-like, prefastened absorbent article prior to packaging the articles.

There are various ways to accomplish the present invention.

For example, the diaper outer cover, or backsheet, and bodyside liner, or topsheet, or both, are constructed to be extendable in the lateral dimension, shown herein as the cross machine direction (CD), and assembled into the precursor diaper. An untensioned elastomeric may be placed in the waist regions of the extendable topsheet or extendable backsheet before joining in the diaper making process, i.e., converting the components into a garment.

Alternatively, the diaper assembly may be produced with the laterally extendible layers and without the waistband elastic, which is subsequently applied. A tensioned or untensioned elastomer, or both, can be applied to the waistband area. In the case where an ungathered waistband is desired, the elastomer will be applied without tension. If a narrowed and gathered elastomeric area is desired, the elastomer will be applied with tension and the elastomeric will gather the cuff area, providing a doubly extendible cuff, with a first stage expansion taking out the gathers, and a second stage expansion expanding the material of the garment body. If both tensioned and untensioned elastomers are applied, a low retractive force may be provided by the tensioned elastomer during initial stretching with a higher retractive force being reached when garment stretch begins stretching the initially untensioned elastomer, thereby providing an extra measure of sealing at the cuff.

A first exemplary embodiment of the present invention would include the precursor web having an extendable topsheet and an extendable backsheet with an elastomeric placed between them in at least one waistband area of the precursor garment. A second exemplary alternative may have a laterally extendable laminate backsheet made of an extendable film and an extendable nonwoven with an elastomeric placed between the extendable layers and in the proper area to be utilized as an elasticized waistband for the resultant garment. Such a laminate backsheet may be comprised of a necked spunbond nonwoven layer laminated by known means to a breathable microporous film with an elastomeric layer placed therebetween prior to the lamination process. Such an elastomeric layer of the laminate backsheet could extend throughout the web if necessary or desired thereby making any area of the laminate backsheet not restrained from lateral expansion by other layers into a potential waistband area.

The methods of the invention permit the use of non-composite elastomerics (e.g., films, meltblown, etc.) in addition to conventional elastomeric materials that require nonwoven facings. In another embodiment, the backsheet or precursor web may be biaxially extendable, i.e., extendable in the lateral and longitudinal directions or to any degree between. In such an embodiment various elastomeric cuffs may be easily formed to operably tension the garment in various axes. For example, in the case of the illustrated diaper, leg cuffs may operably tension the garment along its longitudinal direction, while waist cuffs may operably tension the garment along its lateral direction, all by simply placing elastomers in the cuff areas of the biaxially stretchable precursor webs of the garment.

Further processing advantages may be derived from the present invention when considering that when the waistband of the garment is flat, front or back side panels, or both, may have less skew to their placement to the garment's normal long axis. Consequently, the cross direction dimension of the diaper at the top of the side panel is the same as the cross direction dimension of the diaper at the bottom of the side panel. When the side panels are not skewed, the diaper is easier to apply to a child. Manufacturing is simplified because there is no cross direction tension in the web, and it is easier to take such a diaper and form it into a diaper pant.

BRIEF DESCRIPTION OF THE DRAWINGS

The present invention will be more fully understood and further advantages will become apparent when reference is made to the following detailed description of the invention and the drawings, in which.

DEFINITIONS

For the purposes of the present description, the term "nonwoven web" means a web of fibrous material that is formed without the aid of a textile weaving or knitting process. The term "fabrics" is used to refer to all of the woven, knitted and nonwoven fibrous webs.

As used herein, the terms "elastic", "elastomeric", and forms thereof, mean any material which, in its final form in the completed diaper, upon application of a biasing force, is stretchable, that is, elongatable, and which will substantially return to its original shape upon release of the stretching, elongating force. The term will include precursor elastomerics which are heat activated or otherwise subsequently treated after application to the precursor diaper structure to induce elasticity. By the term "non-elastic," what is meant is that the sheet layers are made from polymers that are generally considered to be inelastic. In other words, use of such inelastic polymers to form the sheet layers would result in sheet layers that are not elastic. The term "extendable" refers to a material which is stretchable in at least one direction but which does not necessarily have sufficient recovery to be considered elastic.

As used herein, the term "machine direction", or MD, means the length of a fabric in the direction in which it is produced. The term "cross machine direction" or CD means the width of fabric, i.e. a direction generally perpendicular to the MD.

Words of degree, such as "about", "substantially", and the like are used herein in the sense of "at, or nearly at" when given the manufacturing and material tolerances inherent in the stated circumstances" and are used to prevent the unscrupulous infringer from unfairly taking advantage of the invention disclosure where exact or figures or absolutes are stated as an aid to understanding the invention.

"Precursor" as used herein means those components, materials, assemblies, or the like which are used or exist in the making of a finished diaper before its completion as a commercially ready product.

"Permanent deformation" as used herein means the changing of the physical structure of the fibers of a web, e.g., a change in molecular orientation and permanent change of length such as achieved by drawing the web.

DETAILED DESCRIPTION OF THE PRESENTLY PREFERRED EMBODIMENTS

The various aspects and embodiments of the invention will be described in the context of disposable absorbent articles, and more particularly referred to, without limitation and by way of illustration only, as a disposable diaper. It is, however, readily apparent that the present invention could also be employed with other absorbent articles, such as feminine care articles, various incontinence garments, medical garments, and any other disposable garments, whether absorbent or not, needing an easily manufactured elastomeric cuff area. Typically, the disposable articles or garments are intended for limited use and are not intended to be laundered or otherwise cleaned for reuse. A disposable diaper, for example, is discarded after it has become soiled by the wearer.

Figure 1:
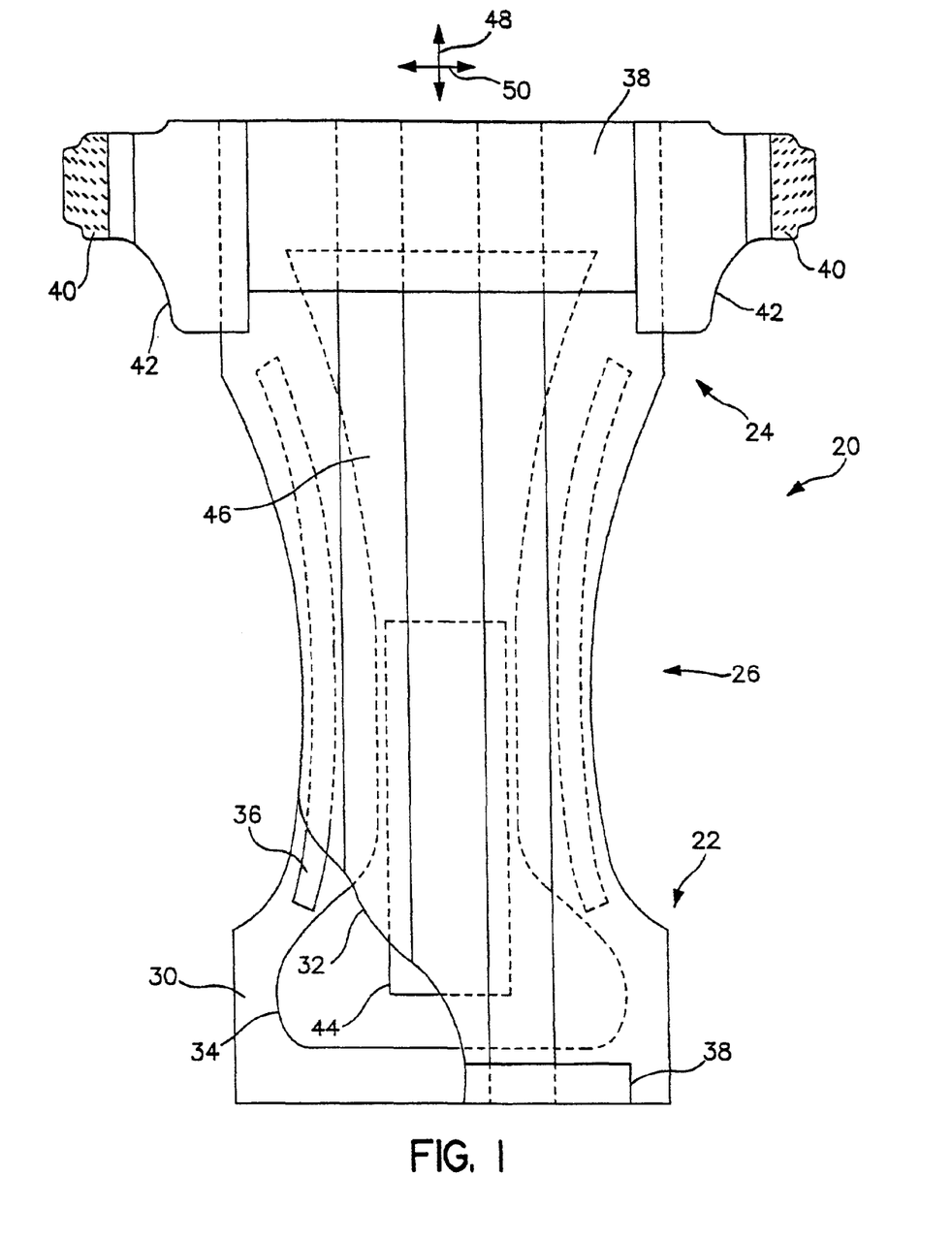
FIG. 1 representatively shows a partially cut-away, top plan view of the inward surface of an example of an article of the invention.

FIG. 1 is a representative plan view of an absorbent article, such as disposable diaper 20, of the present invention in its flat-out, or unfolded state. Portions of the structure are partially cut away to more clearly show the interior construction of diaper 20. The surface of the diaper 20 which contacts the wearer is facing the viewer.

With reference to FIG. 1, the disposable diaper 20 generally defines a front waist section 22, a rear waist section 24, and an intermediate section 26 which interconnects the front and rear waist sections. The front and rear waist sections 22 and 24 include the general portions of the article which are constructed to extend substantially over the wearer's front and rear abdominal regions, respectively, during use. The intermediate section 26 of the article includes the general portion of the article that is constructed to cover the wearer's crotch region and extend between the legs. Thus, the intermediate section 26 is an area where repeated liquid surges typically occur in the diaper or other disposable absorbent article.

The diaper 20 includes, without limitation, an outer cover, or backsheet 30, a liquid permeable bodyside liner, or topsheet, 32 positioned in facing relation with the backsheet 30, and an absorbent body, or liquid retention structure, 34, such as an absorbent pad, which is located between the backsheet 30 and the topsheet 32. The backsheet 30 defines a length, or longitudinal direction 48, and a width, or lateral direction 50 which, in the illustrated embodiment, coincide with the length and width of the diaper 20. The liquid retention structure 34 generally has a length and width that are less than the length and width of the backsheet 30, respectively. Thus, marginal portions of the diaper 20, such as marginal sections of the backsheet 30, may extend past the terminal edges of the liquid retention structure 34. In the illustrated embodiments, for example, the backsheet 30 extends outwardly beyond the terminal marginal edges of the liquid retention structure 34 to form side margins and end margins of the diaper 20. The topsheet 32 is generally coextensive with the backsheet 30 but may optionally cover an area which is larger or smaller than the area of the backsheet 30, as desired.

To provide improved fit and to help reduce leakage of body exudates from the diaper 20, the diaper side margins and end margins may be elasticized according to the present invention with suitable elastic members, as further explained below. For example, as representatively illustrated in FIG. 1, the diaper 20 may include leg elastics 36 which are constructed to operably tension the side margins of the diaper 20 to provide elasticized leg bands which can closely fit around the legs of the wearer to reduce leakage and provide improved comfort and appearance. Waist elastics 38 are employed to elasticize the end margins of the diaper 20 to provide elasticized waistbands. The waist elastics are configured to provide a resilient, comfortably close fit around the waist of the wearer.

Materials suitable for use as the leg elastics 36 and waist elastics 38 are well known to those skilled in the art. Exemplary of such materials are sheets or strands or ribbons of a polymeric, elastomeric material which are adhered to the backsheet, such that elastic constrictive forces are imparted to the backsheet 30. The elastics may also include such materials as polyurethane, synthetic and natural rubber that may optionally be heat shrinkable or heat elasticizable or other materials which may be applied in a pre-elastic form and subsequently treated to impart elasticity. Many variants of elastomeric materials suitable for use with the present invention will occur to the person having ordinary skill in the art upon gaining an understanding of the invention as presented herein.

As is known, fastening means, such as hook and loop fasteners, with the hook portion shown at ref. no. 40, may be employed to secure the diaper on a wearer. Alternatively, other fastening means, such as buttons, pins, snaps, adhesive tape fasteners, cohesives, fabric-and-loop fasteners, or the like, may be employed. In the illustrated embodiment, the diaper 20 includes a pair of side panels 42 to which the fasteners 40 are attached. Generally, the side panels 42 are attached to the side edges of the diaper 20 in one of the waist sections and extend laterally outward therefrom. The side panels 42 may be elasticized or otherwise rendered elastomeric. For example, the side panels 42, or other precursor webs of the garment, may be an elastomeric material such as a neck-bonded laminate (NBL) or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al. Examples of absorbent articles that include elasticized side panels and selectively configured fastener tabs are described in PCT Patent Application No. WO 95/16425 published Jun. 22, 1995 to Roessler; U.S. Pat. No. 5,399,219 issued Mar. 21, 1995 to Roessler et al.; U.S. Pat. No. 5,540,796 to Fries; and U.S. Pat. No. 5,595,618 to Fries.

The diaper 20 may also include a surge management layer 44, located between the topsheet 32 and the liquid retention structure 34, to rapidly except fluid exudates and distribute the fluid exudates to the liquid retention structure 34 within the diaper 20. The diaper 20 may further include a ventilation layer (not illustrated) located between the liquid retention structure 34 and the backsheet 30 to insulate the backsheet 30 from the liquid retention structure 34 to reduce the dampness of the garment at the exterior surface of the backsheet 30. Examples of suitable surge management layers 44 are described in U.S. Pat. No. 5,486,166 to Bishop and U.S. Pat. No. 5,490,846 to Ellis.

As representatively illustrated in FIG. 1, the disposable diaper 20 may also include a pair of containment flaps 46 which are configured to provide a barrier to the lateral flow of body exudates. The containment flaps 46 may be located along the laterally opposed side edges of the diaper 20 adjacent the side edges of the liquid retention structure 34. Each containment flap 46 typically defines an unattached edge which is configured to maintain an upright, perpendicular configuration in at least the intermediate section 26 of the diaper 20 to form a seal against the wearer's body. The containment flaps 46 may extend longitudinally along the entire length of the liquid retention structure 34 or may only extend partially along the length of the liquid retention structure 34. When the containment flaps 46 are shorter in length than the liquid retention structure 34, the containment flaps 46 can be selectively positioned anywhere along the side edges of the diaper 20 in the intermediate section 26. Such containment flaps 46 are generally well known to those skilled in the art. For example, suitable constructions and arrangements for containment flaps 46 are described in U.S. Pat. No. 4,704,96 issued Nov. 3, 1987, to K. Enloe.

The diaper 20 may be of various suitable shapes. For example, the diaper may have an overall rectangular shape, T-shape or an approximately hour-glass shape. In the shown embodiment, the diaper 20 has a generally I-shape. The diaper 20 further has a longitudinal direction 48, and a lateral direction 50. Other suitable components which may be incorporated on absorbent articles of the present invention may include waist flaps and the like which are generally known to those skilled in the art. Examples of diaper configurations suitable for use in connection with the instant invention which may include other components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996 to Hanson et al.

The various components of the diaper 20 are integrally assembled together employing various types of suitable attachment means, such as adhesive, ultrasonic bonds, thermal bonds or combinations thereof. In the shown embodiment, for example, the topsheet 32 and backsheet 30 may be assembled to each other and to the liquid retention structure 34 with lines of adhesive, such as a hot melt, pressure-sensitive adhesive. Similarly, other diaper components, such as the elastic members 36 and 38, fastening members 40, and surge layer 44 may be assembled into the article by employing the above-identified attachment mechanisms.

The illustrated diaper 20 includes a distinctive waistband structure formed by applying an elastomeric 38 to at least the backsheet 30. As known in the art, the backsheet 30 generally includes a fabric or material layer which may be operatively attached or otherwise joined to the other diaper layers to extend over a major portion of the outward surface of the article. According to the present invention, the waistband structure is formed by applying an elastomeric to that layer, or section, of the diaper which is extendible in one or more axes, and especially to a widened lateral dimension, which, if desired, may resume its narrower original lateral dimension upon removal of the widening force. At least portions of the backsheet 30 in the waistband area are not affixed to non-extendible portions of the article or otherwise restricted from extending and contracting. It will occur to the person having ordinary skill in the art that if the backsheet is not used in conjunction with the diaper waistband, other layers used in the construction of a diaper may be similarly utilized according to the precepts of the present invention. Generally, it is desirable for simplicity of construction that the backsheet 30 remains the structural unit of choice for applying the waistband elastomeric in the making of diapers according to the present invention.

Desirably, the neckable backsheet 30 is constructed to be permeable to at least water vapor. For example, in particular embodiments, the neckable backsheet 30 defines a water vapor transmission rate (WVTR) according to the Mocon Water Vapor Transmission Rate Test of at least about 400 g/sq.m/24 hr., desirably at least about 1200 g/sq.m/24 hr, more desirably at least about 2000 g/sq.m/24 hr., and even more desirably at least about 3000 g/sq.m/24 hr. in the non-extended condition. In such embodiments, the neckable backsheet 30 may define a WVTR of from about 400 to about 30,000 g/sq.m/24 hr. Materials which have a WVTR less than those above may not allow a sufficient amount of water vapor diffusion out of the diaper and undesirably result in increased levels of skin hydration. A Mocon WVTR test is described in U.S. Pat. No. 6,156,421 issued Dec. 5, 2000 to Stopper et al.

The backsheet 30 can be composed of various materials that provide the desired property of lateral, or biaxial, expansion when the garment is placed on the wearer. For example, the backsheet 30 can be composed of nonwoven webs such as spunbond fabrics, microporous films, or combinations thereof. In a particular embodiment, the backsheet 30 can be composed of a laminate of two or more layers. For example, the backsheet 30 may be a laminate formed from at least one necked spunbond nonwoven fabric laminated to at least one laterally extendable microporous film material wherein the resultant laminate is extendible in at least the lateral dimension direction of the waistband area. An outer surface of the garment may then be produced with the spunbond facing serving as a fastening material for fabric loop type fasteners.

The backsheet may be elastic or extendable. Suitable nonelastic materials for the extendable backsheet of the present invention include nonwoven webs, woven materials and knitted materials. Nonwoven fabrics or webs have been formed from many processes, for example, bonded carded web processes, meltblown processes and spunbond processes. The non-elastic material is preferably formed from at least one member selected from fibers and filaments of inelastic polymers. Such polymers include polyesters, for example, polyethylene terephthalate; polyolefins, for example, polyethylene and polypropylene; polyamides, for example, nylon 6 and nylon 66. These fibers or filaments are used alone or in a mixture of two or more thereof. Suitable fibers for forming the material include natural and synthetic fibers as well as bicomponent, multi-component, and shaped polymer fibers. Many polyolefins are available for fiber production according to the present invention, for example, fiber forming polypropylenes include Exxon Chemical Company's Escorene® PD 3445 polypropylene and Himont Chemical Company's PF-304. Polyethylenes such as Dow Chemical's ASPUN® 6811A linear low density polyethylene, 2553 LLDPE and 25355 and 12350 high density polyethylene are also suitable polymers. The nonwoven web layer may be bonded to impart a discrete bond pattern with a prescribed bond surface area. Alternative laminate materials that could be used to provide the backsheet 30 of the different aspects of the present invention are described in U.S. patent application Ser. No. 09/460,490 filed Dec. 14, 1999 and entitled "BREATHABLE LAMINATE PERMANENTLY CONFORMABLE TO THE CONTOURS OF A WEARER" or U.S. patent application Ser. No. 09/651,914 filed Aug. 31, 2000 of the same title.

Figure 2:
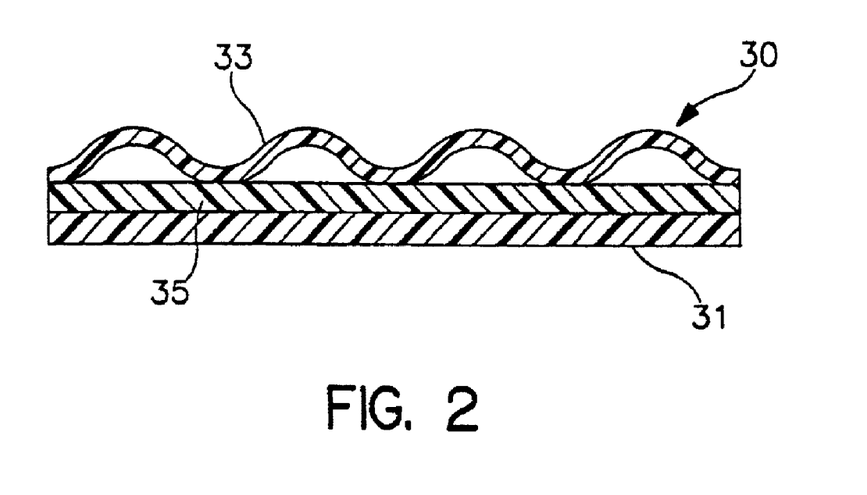
FIG. 2 illustrates an embodiment of a laterally extendable backsheet suitable for use with an embodiment of the present invention.

As seen in FIG. 2, a laterally extendable laminate backsheet 30 made of an extendable film 31 and an extendable nonwoven 33 with an elastomeric 35 placed between the extendable layers 31, 33 and in the proper area to be utilized as an elasticized waistband for the resultant garment. The backsheet is dimensionally stable until subject to a stretching force. Such a laminate backsheet may be comprised of a necked spunbond nonwoven layer laminated by known means to a breathable microporous film with an elastomeric layer placed therebetween prior to the lamination process. Such an elastomeric layer of the laminate backsheet could extend throughout the web if necessary or desired thereby making any area of the laminate backsheet not restrained from lateral expansion by other layers into a potential waistband area.

The topsheet 32, as representatively illustrated in FIG. 1, typically presents a body-facing surface that is compliant, soft-feeling, and non-irritating to the wearer's skin. Further, the topsheet 32 can be sufficiently porous to be liquid permeable, permitting liquid to readily penetrate through its thickness to reach the absorbent composite. A suitable topsheet layer 32 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 32 is typically employed to help isolate the wearer's skin from liquids held in the liquid retention structure 34.

Various woven and nonwoven fabrics can be used for topsheet 32. For example, the topsheet may be composed of a meltblown or spunbond web of the desired fibers, and may also be a bonded-carded-web. Layers of different materials that may have different fiber deniers can also be used. The various fabrics can be composed of natural fibers, synthetic fibers or combinations thereof. The topsheet 32 may be composed of a substantially hydrophobic material, and the hydrophobic material may optionally be treated with a surfactant or otherwise processed to impart a desired level of wettability and hydrophilicity. In a particular embodiment of the invention, the topsheet 32 can be a nonwoven, spunbond polypropylene fabric composed of about 1.0–5.0 denier fibers formed into a web having a basis weight of about 17 gsm and density of about 0.06 gm/cc which will be necked to half its width. The fabric can be surface treated with an operative amount of surfactant, such as known in the art. The surfactant can be applied by any conventional means, such as spraying, printing, brush coating or the like.

Desirably, the topsheet 32 is made from laterally or biaxially extendible materials for compatibility with the backsheet 30 as well as for reduced cost and improved manufacturing efficiency. Suitable laterally extendible materials for use with the present invention may include nonwoven webs, woven materials and knitted materials. Such webs can include one or more fabric layers. Nonwoven fabrics or webs have been formed from many processes, for example, bonded carded web processes, meltblown processes and spunbond processes. The laterally extendible material can be formed from at least one member selected from fibers and filaments of inelastic polymers. Such polymers include polyesters, for example, polyethylene terephthalate, polyolefins, for example, polyethylene and polypropylene, polyamides, for example, nylon 6 and nylon 66. These fibers or filaments are used alone or in a mixture of two or more thereof. Suitable fibers may also include natural and synthetic fibers as well as bicomponent, multi-component, and shaped polymer fibers. Many polyolefins are available for fiber production according to the present invention, for example, fiber forming polypropylenes include Exxon Chemical Company's Escorene® PD 3445 polypropylene and Himont Chemical Company's PF-304. Polyethylenes such as Dow Chemical's ASPUN® 6811A linear low density polyethylene, 2553 LLDPE and 25355 and 12350 high density polyethylene are also suitable polymers. The nonwoven web layer may be bonded to impart a discrete bond pattern with a prescribed bond surface area.

Desirably, both the backsheet 30 and the topsheet 32 are extendible in the lateral direction as set forth above for improved fit and performance of the waistband and the overall garment. The topsheet 32 and backsheet 30 may be connected or otherwise associated together in an operable manner. As used herein, the term "associated" encompasses configurations in which topsheet 32 is directly joined to the backsheet 30 by affixing the topsheet 32 directly to the backsheet 30, and configurations wherein the topsheet 32 is indirectly joined to the backsheet 30 by affixing the topsheet 32 to intermediate members which in turn are affixed to the backsheet 30. The topsheet 32 and the backsheet 30 can, for example, be joined to each other in at least a portion of the diaper periphery by attachment mechanisms (not shown) such as adhesive bonds, sonic bonds, thermal bonds, pinning, stitching or any other attachment techniques known in the art, as well as combinations thereof.

For example, a uniform continuous layer of adhesive, a patterned layer of adhesive, a sprayed pattern of adhesive or an array of separate lines, swirls or spots of construction bonds may be used to affix the topsheet 32 to the backsheet 30. It should be readily appreciated that the above-described attachment mechanisms may also be employed to suitably interconnect, assemble and/or affix together the various other component parts of the garments or articles that are described herein.

The liquid retention structure 34 provides an absorbent structure for holding and storing absorbed liquids and other waste materials, such as the shown absorbent pad composed of selected hydrophilic fibers and high-absorbency particles. The liquid retention structure 34 may also be extendible, not extendible, or elastic, although it should not interfere with the expanding of the waistband area. The liquid retention structure 34 is positioned and sandwiched between the topsheet 32 and backsheet 30 to form the diaper 20. The liquid retention structure 34 has a construction that is generally compressible, conformable, non-irritating to the wearer's skin, and capable of absorbing and retaining body exudates. It should be understood that, for purposes of this invention, the liquid retention structure may be a single, integral piece of material, or alternatively, may have a plurality of individual separate pieces of material which are operably assembled together.

Various types of wettable, hydrophilic fibrous material can be used to form the component parts of liquid retention structure 34. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed. The liquid retention structure 34 can include a matrix of hydrophilic fibers, such as a web of cellulosic fluff, mixed with particles of high-absorbency material. In particular arrangements, the liquid retention structure 34 may include a mixture of superabsorbent hydrogel-forming particles or fibers and synthetic polymer meltblown fibers, or a mixture of superabsorbent particles or fibers with a fibrous coform material including a blend of natural fibers and/or synthetic polymer fibers.

The hydrophilic fibers and high-absorbency particles may be configured to form an average composite basis weight which is within the range of about 400–900 gsm. In certain aspects of the invention, the average composite basis weight may be within the range of about 500–800 gsm, and alternatively may be within the range of about 550–750 gsm to provide desired performance. Ultimately, the average composite basis weight will depend upon the application to which the personal care garment is put and the type and amount of hydrophillic materials.

Optionally, a substantially hydrophilic tissue wrapsheet may be employed to help maintain the integrity of the fibrous structure of the liquid retention structure 34. The tissue wrapsheet is typically placed about the liquid retention structure over at least one major facing surface thereof and composed of an absorbent cellulosic material, such as creped wadding or a high wet-strength tissue that may or may not be pleated. In one aspect of the invention, the tissue wrapsheet can be configured to provide a wicking layer which helps to rapidly distribute liquid over the mass of absorbent fibers including the liquid retention structure 34. The wrapsheet material on one side of the absorbent fibrous mass may be bonded to the wrapsheet located on the opposite side of the fibrous mass to effectively entrap the liquid retention structure 34.

With reference to FIG. 1, each of the leg elastic members 36 can include a plurality of elastomeric strands. Optionally, each leg elastic member may be a composite that includes at least one carrier layer (not shown), and the elastomeric strands can be operatively attached to the carrier layer. Various mechanisms, such as adhesive, thermal bonds, sonic bonds, or the like as well as combinations thereof, can be employed to provide the desired attachments between the elastomeric strands and the carrier layer. For example, each leg elastic member may be composed of a laminate of a plurality of elastomeric strands sandwiched and held between a pair of carrier layers. The carrier layers may desirably be composed of a woven or nonwoven fabric having a basis weight within the range of about 10–50 g/m², but may optionally be composed of a polymer film material.

For example, the carrier layers may be composed of a polypropylene spunbond nonwoven fabric, and the pair of carrier layers may be adhesively bonded together with a suitable pattern of adhesive, such as a swirl-pattern of pressure-sensitive adhesive.

The leg elastic members 36 may have any of a multitude of configurations. For example, the width of the individual elastic members 36 may be varied from about 0.25 millimeters (0.01 inch) to about 38 millimeters (1.5 inch) or more. The elastic members may include a single strand of elastic material, or may include several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the backsheet 30 or topsheet 32, or both, of the diaper 20 in any of several ways that are known in the art. For example, the elastic members may be ultrasonically bonded, heat and pressure sealed using a variety of bonding patterns, or adhesively bonded to the diaper with sprayed or swirled patterns of adhesive. In particular embodiments of the invention, the leg elastic members 36 may include a carrier sheet to which are attached a grouped set of elastics composed of a plurality of individual elastic strands. The elastic strands may intersect or be interconnected, or be entirely separated from each other. The carrier sheet may, for example, include a 0.002 inch thick polymer film, such as a film of unembossed polypropylene material. The elastic strands can, for example, be composed of LYCRA elastomer available from E. I. DuPont de Nemours and Co., a business having offices in Wilmington, Del. Each elastic strand is typically within the range of about 470–1500 decitex (dtx), and may be about 940–1050 dtx. In particular embodiments of the invention, for example, three or four strands can be employed for each elasticized leg band.

Processing Example

The following example is presented to provide a more detailed understanding of the invention. The example is representative, and is not intended to limit the scope of the invention.

Figure 3:
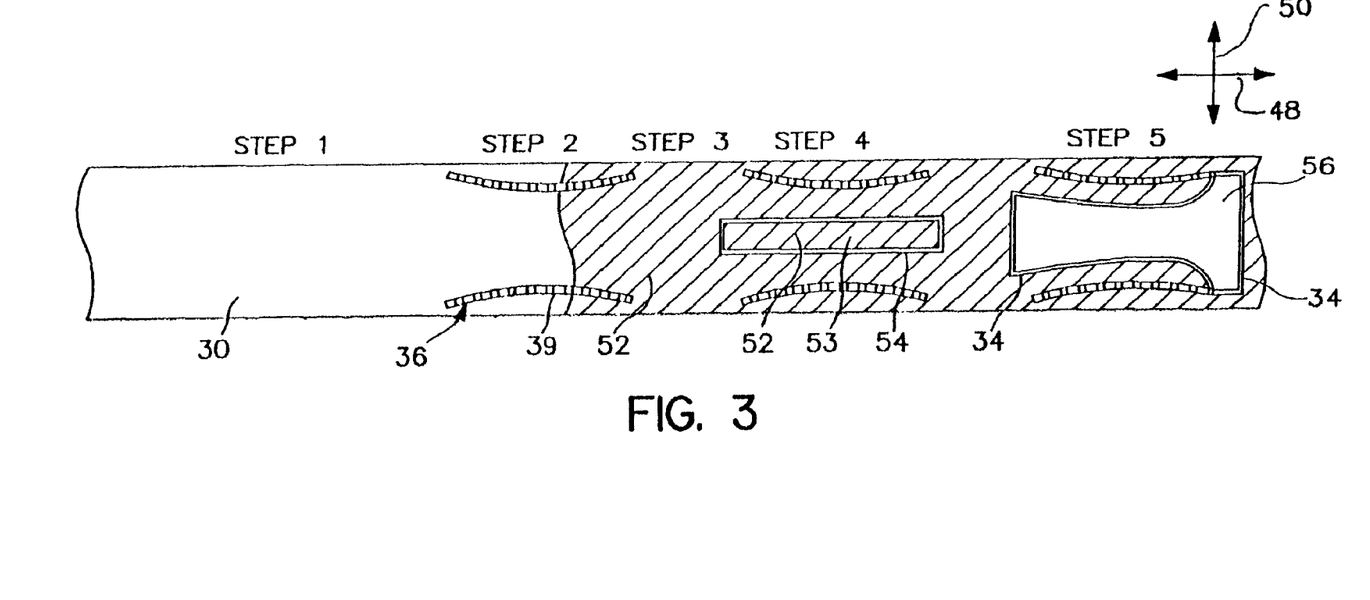
FIG. 3 illustrates a beginning manufacturing sequence of disposable diapers according to the present invention with the longitudinal direction of the diapers being in the machine direction.
Figure 4:
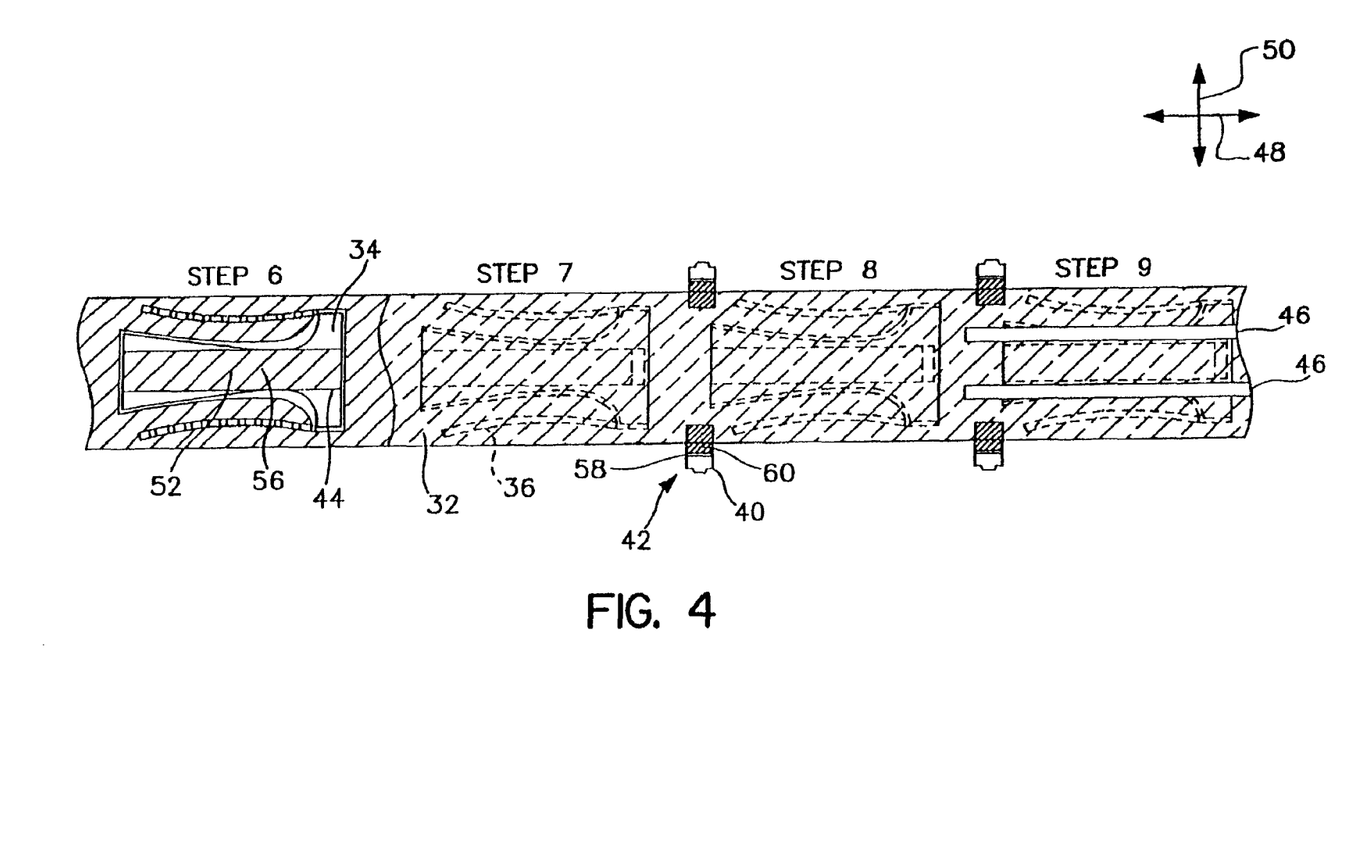
FIG. 4 illustrates a middle manufacturing sequence of disposable diapers according to the present invention with the longitudinal direction of the diapers being in the machine direction.
Figure 5:
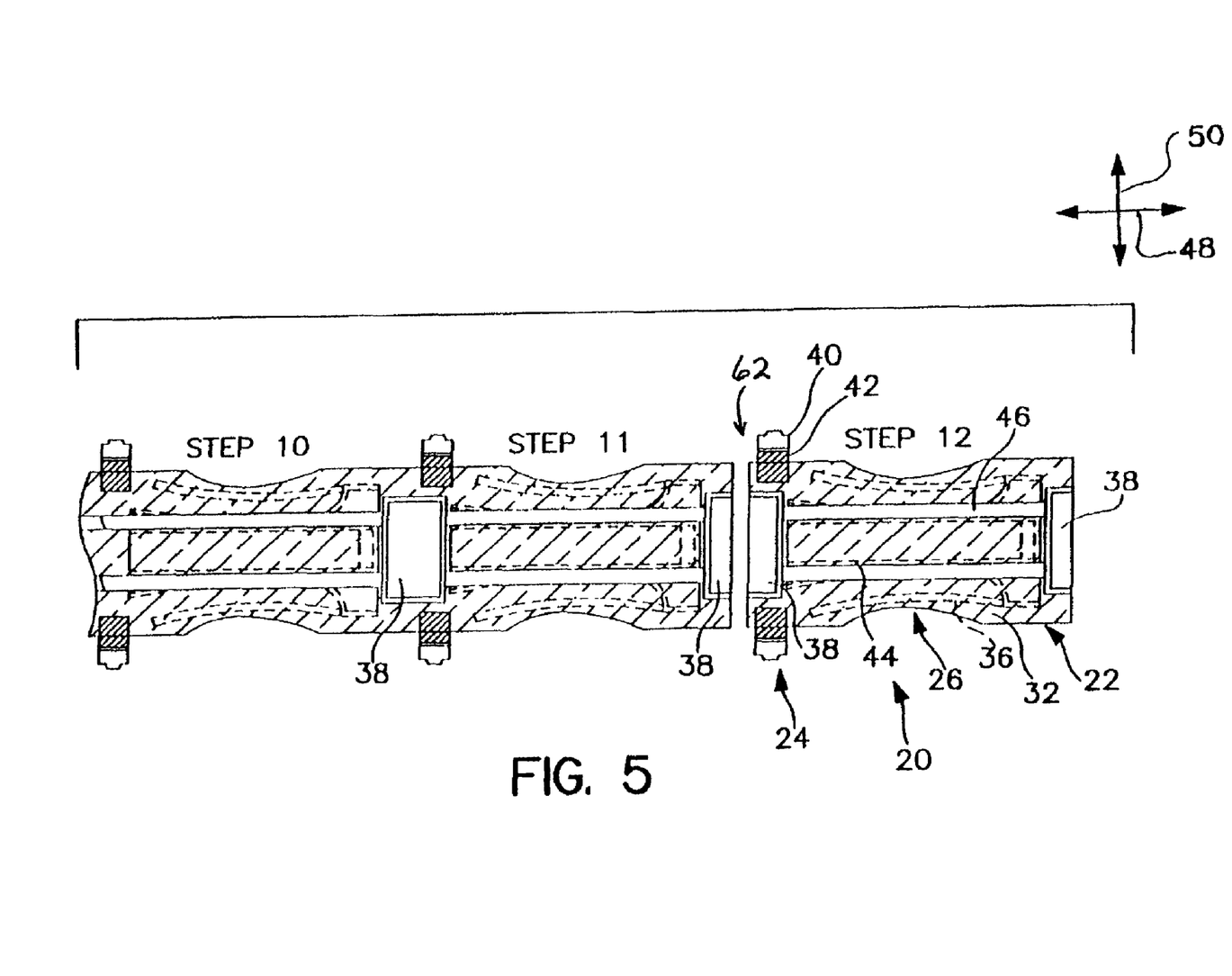
FIG. 5 illustrates an ending manufacturing sequence including the individuation of disposable diapers from the precursor garment assemblage according to the present invention with the longitudinal direction of the diapers being in the machine direction.

With reference to FIGS. 3–5, an exemplary method for constructing an absorbent article such as a disposable diaper according to the present invention may include the steps of constructing a precursor garment web and individuating the diapers therefrom as described below and as illustrated in FIGS. 3–5. While the garments are shown as being constructed with a longitudinal axis in the machine direction, the skilled artisan will appreciate that the techniques of the present invention are not limited to any one axis, cuff area, or particular style of construction.

Referencing FIG. 3, in Step 1 a backsheet web 30 desirably including a material of substantially liquid impermeable and water vapor permeable laminate material according to the above-described embodiment of FIG. 2 is fed into the garment making process as the foundation layer of the precursor garment web. The backsheet material 30 is dimensionally stable but will expand in the lateral direction when force is applied in the lateral direction, and may, if desired, contract in the lateral direction after the force is removed.

In Step 2 tensioned leg elastic members 36 e.g., composed of four LYCRA strands for each leg of Lycra XA Spandex 740 DTEXZ T151 dull (/T-127) and adhesively laminated to a carrier sheet 39, e.g., K-T Slit and Spooled 0.67 mil ALE Carrier Sheet, from KT Industries, Inc. of Winnipeg, Manitoba, Canada, are applied to the top of backsheet material web 30.

In Step 3 an adhesive 52, shown as diagonal lines, e.g., Disposamelt 34-5611, from National Starch & Chemical Co., of Bridgewater, N.J., is applied to the backsheet material 30.

In Step 4 an adhesive 52 e.g., Disposamelt 34-5611, is applied to the top surface 53 of a spacer layer 54, e.g., a 0.8 osy spunbond meltblown spunbond nonwoven which is then applied to the backsheet material 30.

In Step 5 a liquid retention structure 34 e.g., including a composite fluff pad that is approximately a 60/40 blend of a superabsorbent material e.g., Favor SXM-880, from Stockhausen Co. of Greensboro, N.C., and fiberized Fluff Pulp of 16% Hardwood, from Alliance Forest Products, of Coosa Pines, Ala., is applied to the spacer layer 54 or the backsheet material 30. The liquid retention structure 34 may further be covered on its side to be adjacent to topsheet 32 (step 7) with a barrier tissue 56 e.g., American Tissue 12.5 pound white tissue, from American Tissue Corp. of Neenah, Wis. Additionally a forming tissue (not shown) e.g., white 9.79 pound per reel tissue, from American Tissue Corp. of Neenah, Wis., may be positioned to cover the side of Liquid Retention (absorbent) structure 34 adjacent to the backsheet layer 30.

Referencing FIG. 4, in Step 6 a surge management layer 44 e.g., a Through Air Bonded Carded Web nonwoven surge composite for the rapid uptake and channeling of liquids, is located operably adjacent to the liquid retention structure 34. Also in Step 6 an adhesive 52, e.g., Disposamelt 34-5611, is applied to the top surface 56 of the surge management layer 44.

In Step 7 a porous, liquid permeable, and laterally extendible top sheet web 32, indicated by broken cross hatching, is then applied and laminated to the layers of the precursor garment web. In Step 8 the provided side panels 42 having a fastening means 40 e.g., hook material such as VELCRO 851 hook, from Velcro U.S.A. Inc. of Manchester, N.H., and carrier sheet 58 e.g., 1.25 osy SMS, may them be adhesively or ultrasonically laminated, or both, to the precursor garment web.

In Step 9 the containment flaps 46 may be adhesively laminated to the precursor garment web and have elastomeric materials e.g., two elastic strands (not shown) such as Glospan S7 Spandex fiber 700 denier (777 decitex), from Radicspandex (Globe Manufacturing) of Fall River, Mass. The flap elastic strands may be laminated to a nonwoven material e.g., blue SMS 0.65 osy to comprise the flaps 46.

Referencing FIG. 5, in Step 10 untensioned waist elastics 38, e.g., a Necked Bonded laminate may then be applied to the precursor garment web at the waistband regions of the precursor garments to provide for a flat waistband. In other embodiments the elastomeric may be included in one of the precursor layers or otherwise applied before this time. As previously mentioned, the waist elastics 38 may be tensioned and then applied to the precursor garment web to provide for a gathered waistband of extendable material. Leg hole cut outs on the lateral margins of the precursor diaper will be seen as introduced in this step.

In Step 11, the precursor garment is then cut as at 62 into an individual resultant disposable diaper 20 as seen in Step 12. The diaper 20 can then be folded if desired (not shown).

While the invention has been described in detail with respect to specific embodiments thereof, it will be appreciated that those skilled in the art, upon attaining an understanding of the foregoing may readily conceive of alterations to, variations of, and equivalents to these embodiments. Accordingly, the scope of the present invention should be assessed as that of the appended claims and any equivalents thereto.

We claim:

1. A method of producing elastic cuff areas in an absorbent article comprising, a) providing a backsheet web at a first dimension, the backsheet web having a cuff area, the backsheet web expands in a lateral direction to a second dimension when a force is applied and contracts after the force is removed;

b) affixing an untensioned elastic material to the cuff area of the backsheet web when the backsheet web is at the first dimension to provide for a flat cuff area; and c) applying a liquid retention structure to the backsheet web to produce an absorbent article.

2. The method of claim 1 further comprising, associating a laterally extendible topsheet web to the backsheet web and positioning the liquid retention structure between the topsheet and the backsheet web.

3. The method of claim 2 wherein the cuff area is a waistband.

4. The method of claim 2 wherein the cuff area is a leg cuff.

5. The method of claim 1 wherein the backsheet web comprises a microporous film extendable in at least the lateral direction.

6. The method of claim 3 wherein a second elastic material is applied in a tensioned state to the cuff area.

* * * * *